(12) United States Patent
Liu et al.

(10) Patent No.: US 8,642,351 B2
(45) Date of Patent: Feb. 4, 2014

(54) APPARATUS AND METHODS OF FLUID CHROMATOGRAPHY

(75) Inventors: Hongji Liu, Grafton, MA (US); Jeffrey W. Finch, Gig Harbor, WA (US)

(73) Assignee: Waters Technologies Corporation, Milford, MA (US)

( * ) Notice: Subject to any disclaimer, the term of this patent is extended or adjusted under 35 U.S.C. 154(b) by 1136 days.

(21) Appl. No.: 12/441,732

(22) PCT Filed: Sep. 17, 2007

(86) PCT No.: PCT/US2007/078618
§ 371 (c)(1),
(2), (4) Date: Oct. 26, 2009

(87) PCT Pub. No.: WO2008/036586
PCT Pub. Date: Mar. 27, 2008

(65) Prior Publication Data
US 2010/0107742 A1    May 6, 2010

Related U.S. Application Data

(60) Provisional application No. 60/826,248, filed on Sep. 20, 2006.

(51) Int. Cl.
*G01N 30/38* (2006.01)
(52) U.S. Cl.
USPC ........ 436/161; 73/23.41; 73/23.42; 73/61.55; 73/61.56; 210/198.2; 210/656; 422/70; 422/89
(58) Field of Classification Search
USPC ............ 422/70, 89; 436/161; 210/198.2, 656; 73/61.52–61.58, 23.35–23.42
See application file for complete search history.

(56) References Cited

U.S. PATENT DOCUMENTS

| | | | |
|---|---|---|---|
| 3,956,074 A | | 5/1976 | Bittler |
| 4,454,043 A | * | 6/1984 | Ting et al. ............... 210/659 |
| 4,994,165 A | | 2/1991 | Lee et al. |
| 5,117,109 A | * | 5/1992 | Asakawa et al. ......... 250/288 |
| 6,790,361 B2 | | 9/2004 | Wheat et al. |
| 2002/0134142 A1 | * | 9/2002 | Tani et al. ............... 73/61.56 |
| 2004/0035789 A1 | * | 2/2004 | Wheat et al. ............. 210/635 |

(Continued)

OTHER PUBLICATIONS

Pascoe et al, Reduction in Matrix-Related Signal Suppression Effects in Electrospray Ionization Mass Spectrometry Using On-Line Two-Dimensional Liquid Chromatography, Analytical Chemistry, 2001, pp. 6014-6023, vol. 73, No. 24, American Chemical Society.

(Continued)

*Primary Examiner* — Jan Ludlow
(74) *Attorney, Agent, or Firm* — Nielsen IP Law LLC

(57) ABSTRACT

The invention provides improved methods and apparatus for fluid chromatography, and is particularly appropriate to high-pressure liquid chromatography carried out using eluent flow rates less than 1 μl/minute, for example on nanoflow columns. In both single- and multi-dimensional chromatography systems, especially those comprising trapping media to facilitate injection of relatively large volumes of sample on to nanoflow columns, the on-line addition of a diluting solvent enables stronger eluents and sample solvents to be employed without causing premature release of analytes from the trapping media or the degradation of the second dimension chromatographic separation. The invention may be advantageously used for two-dimension reverse phase/reverse phase separations, especially for the separation of complex mixtures of peptides.

47 Claims, 8 Drawing Sheets

(56) References Cited

U.S. PATENT DOCUMENTS

2004/0124128 A1* 7/2004 Iwata .................. 210/198.2
2004/0164025 A1   8/2004 Lewis et al.
2005/0167348 A1* 8/2005 Iwata .................. 210/198.2

OTHER PUBLICATIONS

Grant et al, Generic serial and parallel on-line direct-injection using turbulent flow liquid chromatography/tandem mass spectrometry, Rapid Communications in Mass Spectrometry, 2002, pp. 1785-1792, vol. 16, John Wiley & Sons, Ltd.

Koch et al, On-line clean-up by multidimensional liquid chromatography-electrospray ionization tandem mass spectrometry for high throughput quantification of primary and secondary phthalate metabolites in human urine, Journal of Chromatography, 2003, pp. 169-182, B. 784, Elsevier.

Misl'anova et al, Role of biological matrices during the analysis of chiral drugs by liquid chromatography, Journal of Chromatography, 2003, pp. 91-109, vol. 797, Elsevier.

Nagele et al, Two-dimensional nano-liquid chromatography-mass spectrometry system for applications in proteomics, Journal of Chromatography, 2003, pp. 197-205, vol. 1009, Elsevier.

Allen et al, Isolation of the components of a complex mixture by means of column switching for their enhanced detection by mass spectrometry, Journal of Chromatography, 2001, pp. 209-219, vol. 913, Elsevier.

Zeng et al, A direct injection high-throughput liquid chromatography tandem mass spectrometry method for the determination of a new orally active Xuβ3 antagonist in human urine and dialysate, Rapid Communications in Mass Spectrometry, 2003, pp. 2475-2482, vol. 17, John Wiley & Sons, Ltd.

Zeng et al, High-throughput liquid chromatography for drug analysis in biological fluids: investigation of extraction column life, Journal of Chromatography, 2004, pp. 177-183, vol. 806, Elsevier.

Rogatsky et al, Two-dimensional reverse phase-reverse phase chromatography: A simple and robust platform for sensitive quantitative analysis of peptides by LC/MS. Hardware design, Journal of Separation Science, 2006, vol. 29, pp. 539-546, Wiley-VCH Verlag GmbH & Co. KGaA, Weinheim.

Opiteck et al, Two-Dimensional SEC/RPLC Coupled to Mass Spectrometry for the Analysis of Peptides, Analytical Chemistry, 1997, pp. 2283-2291, vol. 69, No. 13, American Chemical Society.

Jandera et al, Phase system selectivity and two-dimensional separations in liquid column chromatography, Journal of Chromatography, 2005, pp. 112-123, vol. 1087, Elsevier.

Georgi et al, Control of Matrix Effects in Bioanalytical MS/MS using On-line Multidimensional Solid-Phase Extraction, LC/MS Europe, 2004, pp. 2-5, vol. 17 (11a), Advanstar Communications.

Vi et al, A microcapillary trap cartridge-microcapillary high-performance liquid chromatography electrospray ionization emitter device capable of peptide tandem mass spectrometry at the attomole level on an ion trap mass spectrometer with automated routine operation, Rapid Communications in Mass Spectrometry, 2003, pp. 2093-2098, vol. 17, John Wiley & Sons, Ltd.

Davis et al, Automated LC-LC-MS-MS platform using binary ion-exchange and gradient reversed-phase chromatography for improved proteomic analyses, Journal of Chromatography, 2001, pp. 281-291, vol. 752, Elsevier.

Bushey et al, Automated Instrumentation for Comprehensive Two-Dimensional High-Performance Liquid Chromatography of Proteins, Analytical Chemistry, 1990, pp. 161-167, vol. 62, No. 2 American Chemical Society.

Opiteck et al, Comprehensive On-Line LC/LC/MS of Proteins, Analytical Chemistry, 1997, pp. 1518-1524, vol. 69, American Chemical Society.

Shen et al, Automated 20 kpsi RPLC-MS and MS/MS with Chromatographic Peak Capacities of 1000-1500 and Capabilities in Proteomics and Metabolomics, Analytical Chemistry, 2005, pp. 3090-3100, vol. 77, American Chemical Society.

Witold M. Winnik, Continuous pH/Salt Gradient and Peptide Score for Strong Cation Exchange Chromatography in 2D-Nano-LC/MS/MS Peptide Identification for Proteomics, Analytical Chemistry, 2005, pp. 4991-4998, vol. 77, American Chemical Society.

Shen et al, Ultrasensitive Proteomics Using High-Efficiency On-Line Micro-SPE-NanoLC-NanoESI MS and MS/MS, Analytical Chemistry, 2004, pp. 144-154, vol. 76, American Chemical Society.

Davis et al, Determination of Serum Dopamine-β-Hydroxylase Activity by Reverse-Phase Liquid Chromatography with Column Switching, Analytical Chemistry, 1979, pp. 1960-1965, American Chemical Society.

Zhou et al, Quasi-linear Gradients for Capillary Liquid Chromatography with Mass and Tandem Mass Spectrometry, 2000, pp. 432-438, vol. 14, Rapid Commun. Mass Spectrum.

Schachterle et al, Preformed Gradient Technique for Micorbore High-Performance Liquid Chromatography, Analytical Chemistry, 1986, pp. 1368-1372, vol. 58, American Chemical Society.

Schwartz et al, Gradient Elution Chromatography with Micorbore Columns, Analytical Chemistry, 1983, pp. 1752-1760, vol. 55, American Chemical Society.

Berry et al, Low-Cost Liquid Chromatography (LC-LC). IV. "Pulsed Open Tube Gradient Generation", a New Approach for Generating Nanoliter Volume Linear and Tailored Gradients for Capillary Elecrophoresis and Micro-LC, 1990, Journal of Liquid Chromatography, 13(8), pp. 1529-1558, Abstract.

* cited by examiner

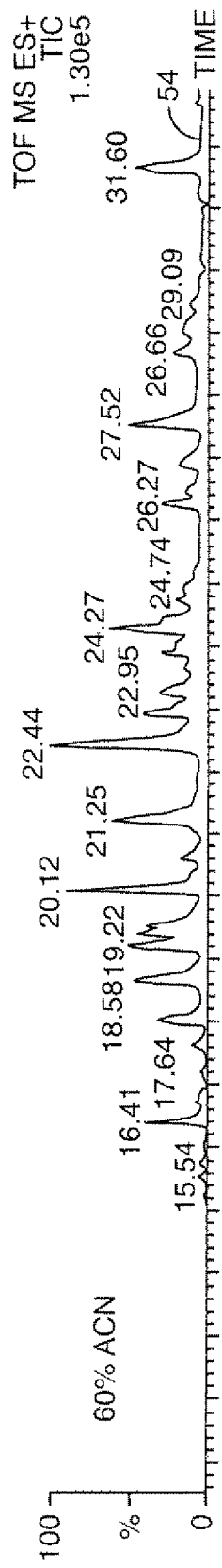
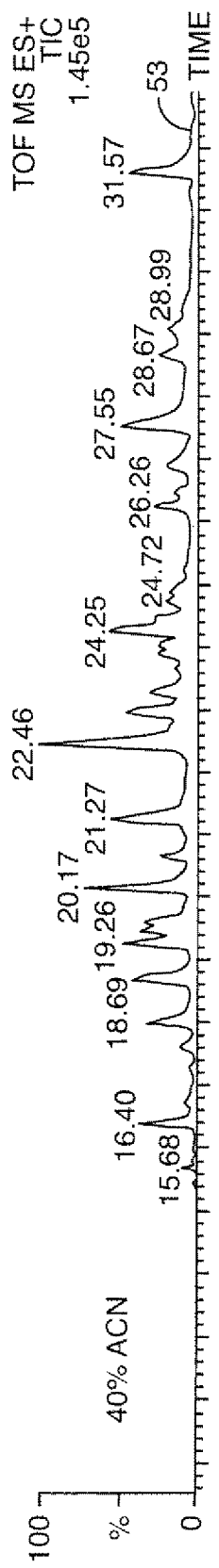
FIG. 5A
FIG. 5B

APPARATUS AND METHODS OF FLUID CHROMATOGRAPHY

CROSS REFERENCE TO RELATED APPLICATIONS

This application claims benefit of and priority to U.S. Provisional Patent Application No. 60/826,248, filed Sep. 20, 2006, the entire contents of which is incorporated herein by reference.

FIELD OF THE INVENTION

This invention relates to fluid chromatography, in particular to high-performance liquid chromatography, and especially reverse-phase liquid chromatography. It also relates to multi-dimensional chromatography, especially involving the use of one or more reverse-phase separation columns, and is particularly useful for the analysis of complex mixtures of peptides and proteins. Particularly preferred embodiments further relate to multi-dimensional reverse-phase chromatography in which one separation column is a nanoflow column for which optimal operation is obtained at flow rates less than 1 µl/minute.

BACKGROUND TO THE INVENTION

In liquid chromatography it is sometimes found that not all the analytes present in a solution sample are eluted from a chromatographic column. This can be especially problematic in the analysis of peptides using reverse-phase chromatography, where the recovery in particular of hydrophobic peptides known to be present in a sample is often found to be incomplete. The term "chromatography column" will be used herein to denote a flow-through device generally cylindrical in shape having a solid phase separation medium therein. That term is used with respect to columns and cartridges. The solid phase separation media may be particulate beads, fibers or monolithic. It has been found that if the sample solution comprises peptides dissolved in a solvent comprising a relatively high proportion of organic solvent (that is, one comprising a low proportion of an aqueous solvent), recovery is greater, but especially in the case of nanoflow chromatography the amount of organic solvent that can be used to dissolve the sample is frequently limited by the detrimental effect that a relatively large amount of a strong solvent may have, especially when analytes have to be trapped.

In multi-dimensional liquid chromatography, similar problems may be encountered due to the incompatibility of the mobile phase used to elute analytes from the first dimension separation media with the mobile phase requirements of the second dimension separation media.

The following two prior techniques of multi-dimensional chromatography are especially relevant to this invention. The first technique uses a strong cation exchange (SCX) column in the first dimension and a C18 reverse phase (RP) column in the second dimension. The second technique uses two reverse-phase columns operated with different solvents to provide different separations on each column. The first technique was described in 1999 and many variations are described in subsequent publications. The earliest version involved the use of a biphasic column comprising two sections, one section comprising an SCX stationary phase and the other comprising a RP stationary phase. In use, a mixture of peptides was first trapped on the SCX portion and subsequently, a series of fractions each comprising a number of peptides, were released from the SCX section to the RP section by injection of a series of "salt plugs" of gradually increasing concentration. Each fraction released underwent separation on the RP section before the next salt plug was injected. Peptides eluted from the RP section were characterised by electrospray mass spectrometry.

More recently, the second technique in which the SCX column is replaced by a second RP column has gained popularity. In such multi-dimensional RP/RP systems a partial separation may be carried out on the first RP column using a basic mobile phase (for example pH 10.0) and the subsequent further separation on the second mobile phase may be carried out using an acidic mobile phase (for example, pH 2.6).

These multi-dimensional separations have been automated and improved by several research groups. Typically, at least the second RP column is a nanoflow column that provides optimum separation at a flow rate of less than µl/minute, and usually at much lower flow rates. To facilitate injection of a large volume sample and to allow desalting of the fractions prior to the second stage separation, a trap column is sometimes provided between the SCX or first RP column and the second RP column.

A limitation on the usefulness of these two-dimensional separation systems, especially the RP/RP systems where different mobile phases must be used for each stage to provide different types of separation, is the potential incompatibility of the mobile phase used for the first stage separation with that required for the second stage separation. Limitations may also be imposed on the nature of the solvent used to dissolve a sample even with a single-dimensional separation, especially with nanoflow chromatography where the injected sample volume may be large in comparison with the volume of elution solvent used for a separation. A variety of prior techniques for mitigating these problems have been described, usually involving the intermediate trapping of samples either on a separate trap column or on a column used in a multidimensional separation, or by modifying the solvents used for the elution. However, these are usually of limited application and few, if any, are suitable for use with nanoflow columns.

SUMMARY OF THE INVENTION

It is an object of the invention to provide methods and apparatus for improving fluid chromatography, especially liquid chromatography using nanoflow columns and multi-dimensional liquid chromatography. It is another object of the invention to provide methods and apparatus for extending the range of mobile phases and sample solvents that can be used in multi-dimensional liquid chromatography. It is a further object of the invention to provide methods and apparatus that extend the range of sample solvents that can be used with single-dimensional chromatography, particularly nanoflow chromatography. It is a yet further object of the invention to provide apparatus and methods of fluid chromatography which increase the recovery of analytes present in a sample, especially in single- or multi-dimensional reverse-phase chromatography, and especially when used for the analysis of proteins and peptides.

In accordance with these objectives the invention provides a method of separating analytes in a sample that comprises one or more analytes dissolved in a sample solvent. The method comprises introducing an aliquot of the sample into a flow of an eluent to form a flow of an analyte-bearing eluent. Next, the method comprises adding to the flow of analyte-bearing eluent a flow of a diluting solvent, different from the sample solvent, to form a flow of a diluted analyte-bearing eluent. Next, at least some of the flow of diluted analyte-bearing eluent is passed into chromatographic separation means to separate the one or more analytes.

The invention may further provide a method of separating analytes in a sample that comprises one or more analytes dissolved in a sample solvent. The method comprises introducing an aliquot of the sample into a flow of an eluent to form a flow of a first analyte-bearing eluent. Next, the method comprises the step of adding to the flow of first analyte-bearing eluent a flow of a diluting solvent, different from said sample solvent, to form a flow of a diluted analyte-bearing eluent. Next, at least some of the flow of diluted analyte-bearing eluent is passed into analyte-trapping means to trap therein at least one the analytes. Next, at least a releasing solvent is introduced into the analyte trapping means to release at least one analyte trapped therein and to form a flow of a second analyte-bearing eluent. Next, at least some of the flow of second analyte-bearing analyte is passed into chromatographic separation means to separate the one or more analytes.

Conveniently, methods of the invention may comprise changing the composition with time of at least one of the eluent, the diluting solvent, and/or the releasing solvent so that a gradient elution takes place on the chromatographic separation means. One solvent is organic, and the gradient elution increases the proportion of the organic solvent.

For example, in the case of a nanoflow reverse-phase column operated with a solvent gradient starting with a weak aqueous solvent, analyte-trapping means comprising a short trap column is typically provided upstream of the main column on which trap column analytes may be trapped prior to their admission to the nanoflow column. The trap column typically is larger diameter than the nanoflow column, thereby allowing a greater flow of mobile phase to pass through it. In use, a sample is loaded on the trap column at a relatively high flow rate using an auxiliary pump while the output of the trapping column is diverted to waste. Once all the analytes have been trapped, a binary high-pressure pump may be used to elute the trapped analytes to the main nanoflow column and to perform a separation. The inventors have found that in the case of a reverse-phase separation, the solvent used to carry the analytes to the trap column must be relatively weak (that is, have a limited organic content) because use of too strong a solvent tends to cause the analytes to be prematurely eluted from the trap. It has been observed that if the sample solvent is too weak, however, the recovery of peptides known to be present in a sample is often incomplete. Unfortunately, although recovery can be increased by use of a stronger solvent, it is not usually possible to use a sufficiently strong solvent without causing premature release of at least some peptides from the trap. By adding an aqueous diluting solvent to the solvent flow as described, it has been found that a stronger sample solvent can be used while analytes are still effectively trapped, thereby improving the recovery of peptides.

Typically, a solvent gradient is employed to carry out the main separation on the nanoflow column. In use, therefore, the solvent gradient acts as a releasing solvent to release the analytes from the trap column. In an alternative embodiment, however, a releasing solvent is provided by injecting aliquots of a suitable releasing solvent into the flow of solvent used for carrying out the separation. Such a method is useful in the case where the trap column is an SCX column, where a series of aliquots of salt solutions of increasing strength can be injected to release in turn different groups of trapped peptides from the trap column.

In another embodiment, the invention features a method of multi-dimensional chromatography, wherein a chromatography column in effect replaces the trap column discussed above. Thus, the invention provides a method of separating analytes in a sample that comprises one or more analytes dissolved in a sample solvent. The method comprises introducing an aliquot of a sample into a flow of an eluent to form a flow of a first analyte-bearing eluent. Next, the method comprises the step of passing at least some of the flow of analyte-bearing eluent through first chromatographic separation means to form a flow of an intermediate eluate. Meanwhile, a diluting solvent is added to at least some of the flow of intermediate eluate to form a flow of a diluted intermediate eluate. Next, at least some of the diluted intermediate eluate is passed into second chromatographic separation means. Such a method is performed in a similar manner to the method described above, except that the first chromatographic separation means replaces the analyte-trapping means. Conveniently, the method is operated in a "heart-cutting" mode, passing at least one group of analytes eluting from the first chromatographic separation means to the second chromatographic separation means. Addition of the diluting solvent to the intermediate eluent from the first separation means then increases recovery of the analytes eluted from the first separation means by the solvent used for the first separation means.

Another embodiment of the invention features a method of separating analytes in a sample that comprises one or more analytes dissolved in a sample solvent. The method comprises introducing an aliquot of a sample into an eluent to form a first analyte-bearing eluent. The method comprises the step of passing at least some of the first analyte-bearing eluent through first chromatographic separation means to form a flow of an intermediate eluate. Meanwhile, a diluting solvent is added to the flow of intermediate eluate to form a flow of a diluted intermediate eluate. Next, at least some of the diluted intermediate eluate is passed through analyte trapping means to trap at least one of the analytes. Next, at least a releasing solvent is passed into the analyte trapping means to release at least one analyte trapped therein and to form a flow of a second analyte-bearing eluent. Next, at least some of the second analyte-bearing eluent is passed into second chromatographic separation means. In this method, an analyte-trapping means (typically a short reverse-phase column capable of operation at a relatively high flow rate) is provided between the first chromatographic separation means and the second chromatographic separation means. A preferred second separation means is a nanoflow column. One embodiment provides a SCX or an RP column for the first separation means and a reverse-phase nanoflow column for the second separation means. Gradient elution may be carried out on either or both of the first and second separation means. The eluate from the analyte-trapping means may be diverted to waste while analytes are trapped, as explained above. With a suitable arrangement of valves and pumps, methods according to the invention allow a separation to be continued on the second separation means while analytes are being separated on the first separation means or are being trapped.

The method is useful when a reverse-phase separation is being carried out on the second separation means while a strong solvent is eluting from the first separation means. The addition of a weak (aqueous) diluting solvent prevents premature release of analytes from the analyte-trapping means in a manner similar to that described.

The releasing solvent comprises a solvent gradient also used to elute analytes from the second separation means. Alternatively, aliquots of a suitable solvent (or salt solutions, in the case of an SCX column used for the first separation means) are injected to provide solvents of different strengths to release different fractions of analytes for the analyte-trapping means.

The invention also provides apparatus for separating analytes in a sample that comprises one or more analytes dissolved in a sample solvent. The apparatus comprises means for delivering a flow of an eluent and means for introducing a said sample into the flow of eluent to form a flow of an analyte-bearing eluent. The apparatus further comprises means for adding to the flow of analyte-bearing eluent a flow of a diluting solvent, different from said sample solvent, to form a flow of diluted analyte-bearing eluent, and chromatographic separation means disposed to receive at least some of the flow of diluted analyte-bearing eluent to separate the one or more analytes. Preferably the means for delivering a flow of eluent and the means for delivering a flow of a diluting solvent comprise high-pressure fluid pumps, typically of the type used for high-pressure liquid chromatography. The chromatographic separation means comprise a liquid-chromatography column suitable for separating the analytes comprised in the sample, especially a reverse-phase nanoflow column for operation at an eluent flow rate of less than 1 µl/minute. In such a case either or both of the pumps delivering eluent of diluting solvent may comprise a binary pump capable of providing a solvent whose composition changes with time, allowing a gradient elution preferably to be carried out on the chromatographic column. Such a reverse-phase gradient elution commences with a weak solvent comprising a low proportion of organic solvent and a high proportion of aqueous solvent, and gradually increases in strength (increasing proportion of organic solvent) as the elution proceeds. The invention provides a diluting solvent comprising a high proportion of an aqueous solvent. This is especially appropriate when a large volume of a sample solution comprising analytes dissolved in a sample solvent comprising a high proportion of an organic solvent is injected into the flow of eluent. The addition of an aqueous diluting solvent mitigates the effect of the sample solvent causing a temporary increase in solvent strength as it reaches the column at the start of the separation, which in the absence of the diluting solvent can cause premature elution of the analytes. The invention therefore enables the use of a sample solvent comprising a higher proportion of an organic solvent than would otherwise be possible, and the inventors have found that so doing typically increases the proportion of analytes which can be recovered in a sample comprising a large number of peptides and proteins.

Preferably, the invention is be used in conjunction with chromatographic separation means comprising a normal-phase column using a gradient elution commencing with a high proportion of organic solvent. In such a case, the diluting solvent comprises a high proportion of organic solvent, which mitigates a detrimental effect that an aqueous sample solvent may otherwise have on the separation. Similarly, addition of a suitable diluting solvent mitigates the effect of an eluent comprising a high proportion of salts or buffers.

Another embodiment of the invention features apparatus for separating analytes in a sample that comprises one or more analytes dissolved in a sample solvent. The apparatus comprises means for delivering a flow of an eluent, means for introducing a sample into the flow of eluent to form a flow of a first analyte-bearing eluent, and means for adding to the flow of first analyte-bearing eluent a flow of a diluting solvent, different from the sample solvent, to form a flow of diluted analyte-bearing eluent. The apparatus further comprises analyte-trapping means disposed to receive at least some of the flow of diluted analyte-bearing eluent to trap therein at least one of the analytes, and means for introducing at least a releasing solvent into the analyte-trapping means to release at least one of the analytes trapped therein to form a flow of a second analyte-bearing eluent. The apparatus further comprises chromatographic separation means disposed to receive at least some of the flow of second analyte-bearing eluent to separate the one or more analytes. Programmable control means refers to a central processing unit (CPU), computer, microprocessor, or other suitable microelectronic device. Such control means is for controlling the means for delivering a flow of eluent, the means for introducing a sample, the means for adding a diluting solvent, and means for introducing a releasing sample. As in the previous embodiment, the means for delivering a flow of eluent and the means for adding a flow of diluting solvent comprise high-pressure liquid-chromatography pumps, at least one of which may be a binary pump capable of generating a flow of solvent whose composition changes with time.

Preferably, the chromatographic separation means comprises a chromatographic column, for example a reverse-phase nanoflow column for operation at a flow rate of less than 1 µl/minute, and the analyte-trapping means comprises a short reverse-phase column capable of operation at a higher flow rate and of trapping at least some of the analytes in a s sample.

Preferably, the apparatus further comprises means for diverting to waste at least some of the eluate from the analyte trapping means while analytes are being trapped in the analyte-trapping means. Such means comprise conduits and a valve under the control of the programmable control means, which directs flow from the analyte-trapping means to waste or to the chromatographic separation means as required. This arrangement allows analytes in a sample to be trapped using a flow of eluent much greater than that required for a subsequent separation on the chromatographic separation means while the eluate from the trapping means is diverted to waste, thereby permitting the use of larger sample volumes than would be possible if samples were to be directly introduced into the very low flow rate required for the subsequent chromatographic separation. Once the analytes have been trapped, the flow rate through the trapping means is reduced to that required for the separation, and the eluate from the analyte-trapping means is then directed to the chromatographic separation.

Preferably, the sample solvent should not prematurely release analytes from the analyte-trapping means before the releasing solvent is introduced. The addition of the diluting solvent permits the use solvents that could not otherwise be used, as described. Such apparatus may be used to permit the use of a sample solvent having a high proportion of organic solvent in the case of a reverse-phase gradient elution on a nanoflow reverse-phase column and reverse-phase analyte-trapping means.

As used herein, means for introducing a sample into the flow of eluent refers to valves configured to introduce a fixed volume of sample solution from a loop. The valves may be controlled by the programmable control means. Alternatively, the means for introducing a sample may comprise an autosampler or a septum device through which a sample can be introduced from a syringe.

As used herein, means for introducing at least a releasing solvent, refers to one or more pumps, and, in particular, binary high-pressure fluid pumps capable of providing a flow of solvent whose composition changes with time. A programmable control means is programmed to cause it to generate a flow of releasing solvent whose composition changes with time. This enables the releasing solvent to elute analytes from the chromatographic separation means as well as release analytes from the analyte-trapping means. The term, "means for adding a flow of diluting solvent" refers to a pump, and, in particular, a binary high-pressure fluid pump. The programmable control means is programmed to provide a flow of diluting solvent while analytes are being trapped the analyte-trapping means and to provide a flow of releasing solvent when analytes are being released from the analyte-trapping means and passed to the chromatographic separation means. As used herein, the term "means for delivering an eluent" means one more pumps, and in particular an auxiliary pump capable of delivering a single solvent suitable for transporting the analytes comprised in the sample solvent to the analyte-trapping means.

As preferred, means for delivering an eluent is a binary fluid pump capable of delivering fluid through said analyte trapping means to the chromatographic separation means to allow a chromatographic separation of at least some of said analytes to be carried out. The programmable control means is programmed to cause the means for delivering the flow of diluting solvent to discontinue the addition of a diluting solvent after at least some analytes have been trapped in the analyte trapping means. Preferably, the means for delivering a flow of diluting solvent is an auxiliary single solvent pump.

One embodiment of the present invention features multi-dimensional chromatography. An apparatus, having features of the present invention comprises means for delivering a flow of an eluent, means for introducing a said sample into the flow of eluent to form a flow of a first analyte-bearing eluent, and first chromatographic separation means disposed to receive at least some of the flow of first analyte-bearing eluent to form a flow of an intermediate eluate. The apparatus further comprises means for adding to the flow of intermediate eluate a flow of a diluting solvent to form a flow of diluted intermediate eluate and analyte-trapping means disposed to receive at least some of the flow of diluted intermediate eluate to trap therein at least one of said analytes. The apparatus further comprises means for introducing at least a releasing solvent into the analyte-trapping means to release at least one of the analytes trapped therein and to form a flow of a second analyte-bearing eluent, and second chromatographic separation means disposed to receive at least some of the flow of second analyte-bearing eluent and to separate the one or more analytes.

Preferably, the apparatus comprises programmable control means and means for diverting to waste at least some of the eluate from the analyte-trapping means while analytes in the intermediate eluate are being trapped. In related embodiments the second chromatographic separation means comprises a nanoflow reverse-phase column and the first chromatographic separation means may comprise a chromatographic column capable of operation at higher flow rates. The analyte-trapping means may comprise a column similar in properties to the second chromatographic separation means but capable of operation at higher flow rates. Preferably, the apparatus comprises means for diverting to waste at least some of the eluate from the analyte-trapping means while analytes are being trapped.

Preferably, the means for delivering a flow of eluent is a an eluent pump, such as a binary high-pressure pump, and the programmable control means is programmed to cause the eluent pump to generate a flow of eluent having a composition such that at least some analytes comprised in a sample introduced into the flow of eluent undergo separation on the first chromatographic separation means before passing into the intermediate eluate.

Preferably, the analyte-trapping means is a reverse-phase separation media and the means for adding a flow of diluting solvent is a pump for delivering a flow of an aqueous solvent. The second chromatographic separation media is reverse-phase separation media and may be a nanoflow column. Addition of an aqueous diluting solvent prevents premature release of analytes trapped in the analyte-trapping means by eluate from the first chromatographic separation means, either because of the nature of the eluent used or because of the elution of a slug of sample solvent. The invention therefore allows the use of a greater range of sample solvents or eluents for the first chromatographic separation means.

Preferably, the means for adding a flow of diluting solvent comprises a is pump, in particular a binary high-pressure fluid pump.

The programmable control means is programmed to cause the binary high-pressure pump to provide a flow of diluting solvent while analytes are being trapped in said analyte-trapping means and to provide a flow of releasing solvent when analytes are being released from said analyte-trapping means and passed to said second chromatographic separation means. The same binary high-pressure pump may also be used to provide the flow of releasing solvent when required. To enable this, the programmable control means is programmed to cause the pump to deliver a flow of releasing solvent whose composition changes with time so that the releasing solvent may also be used to carry out a separation of analytes on the second chromatographic separation means as well as to release analytes from the analyte-trapping means.

Preferably, in multi-dimensional embodiments, the programmable control means is programmed for one or more of the following steps.

a) to cause the means for delivering a flow of eluent to deliver eluent of a first strength to the first chromatographic separation means so that a first group of analytes present in a the sample may be eluted from the first chromatographic separation means and trapped in the analyte-trapping means;

b) to cause the means for adding a flow of diluting solvent to add a diluting solvent while the first group of analytes are being trapped in the analyte-trapping means;

c) to cause the means for introducing a releasing solvent to introduce a releasing solvent into the analyte-trapping means once the first group of analytes have been trapped therein, and to separate at least some of the first group of analytes on the second chromatographic separation means;

d) after at least some of the first group of analytes have passed through the second chromatographic separation means, to cause the means for delivering a flow of eluent to deliver eluent of a second strength so that a second group of analytes previously present in the first chromatographic separation means may be eluted from the first chromatographic separation means and trapped in the analyte-trapping means;

e) to cause the means for adding a flow of diluting solvent to add a diluting solvent while the second group of analytes are being trapped in the analyte-trapping means;

f) to cause the means for introducing a releasing solvent to introduce a releasing solvent into the analyte-trapping means once the second group of analytes have been trapped therein, and to separate at least some of the second group of analytes on the second chromatographic separation means.

Where an eluent pump is provided as described, in another embodiment the programmable control means is programmed for one or more of the following steps:

a) to cause the eluent pump to deliver eluent of a first strength to the first chromatographic separation means so that a first group of analytes present in a the sample may be eluted from the first chromatographic separation means and trapped in the analyte-trapping means while the eluate from the analyte-trapping means is diverted to waste;

b) to cause the binary high-pressure fluid pump to add a diluting solvent while the first group of analytes are being trapped in the analyte-trapping means;

c) after the first group of analytes have been trapped in the analyte-trapping means, to cause the binary high-pressure pump to introduce a releasing solvent into the analyte-trapping means while the eluate from the analyte-trapping means is directed to the second chromatographic separation means;

d) to cause the binary high-pressure pump to change the composition of the releasing solvent to separate at least some of the first group of analytes on the second chromatographic separation means;

e) after at least some of the first group of analytes have passed through the second chromatographic separation means, to cause the eluent pump to deliver eluent of a second strength so that a second group of analytes previously present in the first chromatographic separation means may be eluted from the first chromatographic separation means and trapped in the analyte-trapping means while the eluate from the analyte-trapping means is diverted to waste;

f) to cause the binary high-pressure fluid pump to add a diluting solvent while the second group of analytes are being trapped in the analyte-trapping means, g) after the second group of analytes have been trapped in the analyte-trapping means, to cause the binary high-pressure pump to introduce a releasing solvent into the analyte-trapping means while the eluate from the analyte-trapping means is directed to the second chromatographic separation means;

h) to cause the binary high-pressure pump to change the composition of the releasing solvent to separate at least some of the second group of analytes on the second chromatographic separation means.

The invention may further provide apparatus as described wherein the programmable control means is programmed for one or more of the following steps:

a) to cause the means for delivering a flow of eluent to deliver eluent of a predetermined strength to the first chromatographic separation means;

b) while the eluate from the analyte-trapping means is diverted to waste, to cause the means for introducing a sample to introduce a sample comprising at least a first and a second group of analytes into the flow of eluent so that the first and the second groups of analytes may be separated from one another on the first chromatographic separation means and only the first group of analytes may be eluted and trapped in the analyte-trapping means;

c) to cause the means for adding a flow of diluting solvent to add a diluting solvent while the first group of analytes are being trapped in the analyte-trapping means;

d) to cause the means for introducing a releasing solvent to introduce a releasing solvent into the analyte-trapping means once the first group of analytes have been trapped therein and to separate at least some of the second group of analytes on the second chromatographic separation means;

e) after at least some of the first group of analytes have passed through the second chromatographic separation means and while the eluate from the analyte trapping means is diverted to waste, to cause the means for introducing a sample to introduce into the flow of eluent an aliquot of a different solvent to increase the strength of the eluent so that second group of analytes may be eluted from the first chromatographic separation means and trapped in the analyte-trapping means;

f) to cause the means for adding a flow of diluting solvent to add a diluting solvent while the second group of analytes are being trapped in the analyte-trapping means;

g) to cause the means for introducing a releasing solvent to introduce a releasing solvent into the analyte-trapping means once the second group of analytes have been trapped therein, and to separate at least some of the second group of analytes on the second chromatographic separation means.

Where an eluent pump is provided as described, the invention may provide apparatus wherein the programmable control means is programmed:

a) to cause the eluent pump deliver eluent of a predetermined strength to the first chromatographic separation means;

b) while the eluate from the analyte-trapping means is diverted to waste, to cause the means for introducing a sample to introduce a sample comprising at least a first and a second group of analytes into the flow of eluent so that the first and the second groups of analytes may be separated from one another on the first chromatographic separation means and only the first group of analytes may be eluted and trapped in the analyte-trapping means;

c) to cause the binary high-pressure fluid pump to add a diluting solvent while the first group of analytes are being trapped in the analyte-trapping means;

d) after the first group of analytes have been trapped in the analyte-trapping means, to cause the binary high-pressure pump to introduce a releasing solvent into the analyte-trapping means while the eluate from the analyte-trapping means is directed to the second chromatographic separation means;

e) to cause the binary high-pressure pump to change the composition of the releasing solvent to separate at least some of the first group of analytes on the second chromatographic separation means;

f) after at least some of the first group of analytes have passed through the second chromatographic separation means and while the eluate from the analyte-trapping means is diverted to waste, to cause the means for introducing a sample to introduce into the flow of eluent an aliquot of a different solvent to increase the strength of the eluent so that second group of analytes may be eluted from the first chromatographic separation means and trapped in the analyte-trapping means;

g) to cause the binary high-pressure fluid pump to add a diluting solvent while the second group of analytes are being trapped in the analyte-trapping means, h) after the second group of analytes have been trapped in the analyte-trapping means, to cause the binary high-pressure pump to introduce a releasing solvent into the analyte-trapping means while the eluate from the analyte-trapping means is directed to the second chromatographic separation means;

i) to cause the binary high-pressure pump to change the composition of the releasing solvent to separate at least some of the second group of analytes on the second chromatographic separation means.

BRIEF DESCRIPTION OF THE FIGURES

FIG. 5A-5D depict results obtained for the separation of a sample comprising an enolase digest using the apparatus shown in FIG. 2 as measured as total ion count by time of flight mass spectrometer as acetylnitrate concentration is changed from 60 to 0%.

DETAILED DESCRIPTION OF EMBODIMENTS OF THE INVENTION

Figure 1:
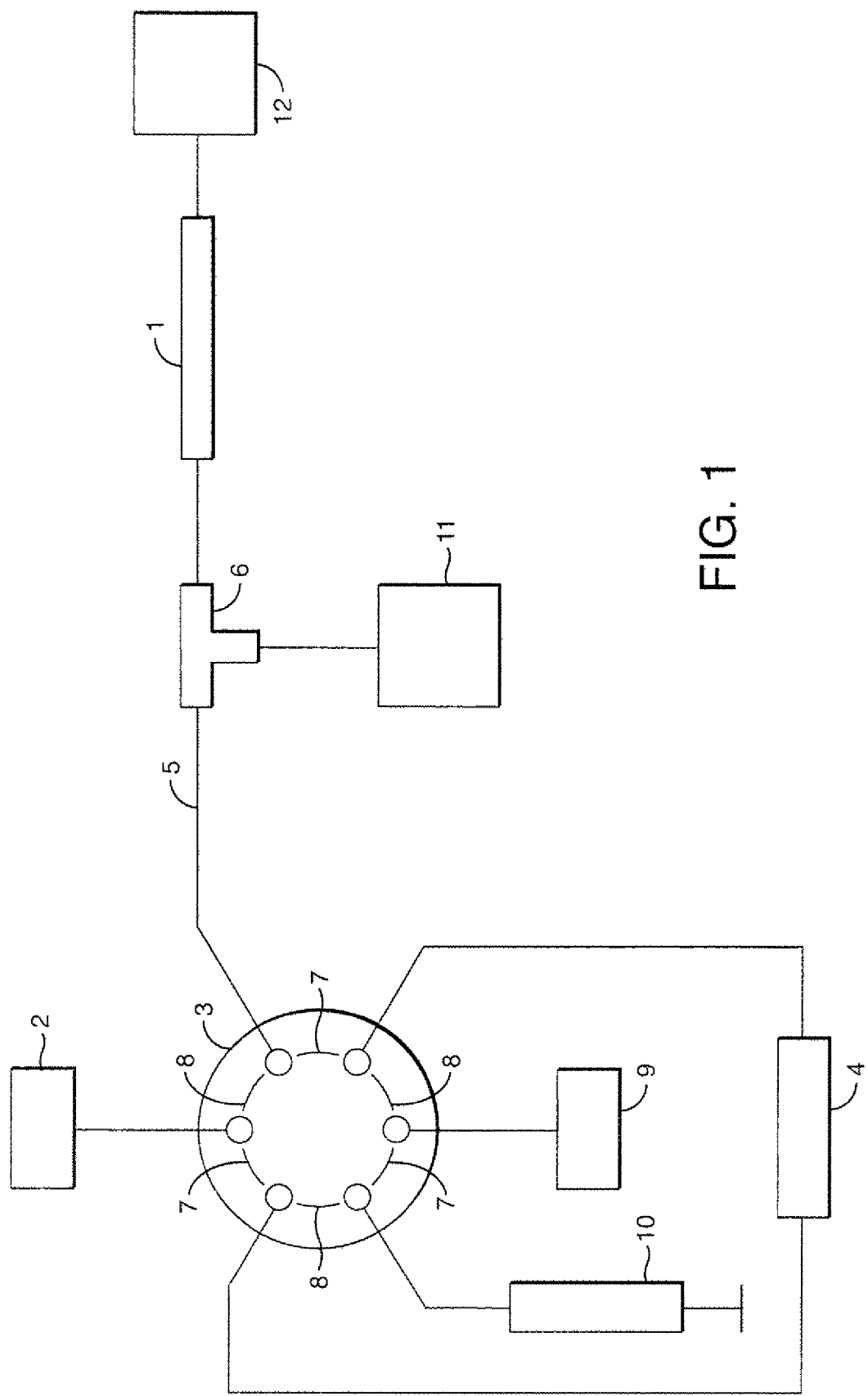
FIG. 1 is a schematic drawing of apparatus according to a first embodiment of the invention.

Referring first to FIG. 1, an embodiment of the invention comprising a single chromatographic separation means (for example, a C18 reverse-phase nanoflow column 1, capable of separating analytes present in a sample) is supplied with eluent from a means for delivering a flow of eluent (a binary high-pressure liquid chromatography pump 2.) Means for introducing a sample solution comprising analytes into the flow of eluent comprises a six-port sample valve 3 fitted with a sample loop 4. The valve 3 is connected between the pump 2 and a feed pipe 5 that connects to the column 1 via a T-connector 6. Valve 3 has a "run" position wherein its ports are connected as indicated by the links 7 and a "load" position in which its ports are connected as indicated by the links 8. In the "run" position, pump 2 is connected via the sample loop 4 to the feed pipe 5 so that eluent from the pump sweeps out a sample previously loaded into the loop 4 and carried it to the column 1. A sample solution (comprising analytes dissolved in a sample solvent) contained in a reservoir 9 may be introduced into the loop 4 by means of a syringe 10 with valve 3 in the "load" position. Alternatively, a conventional autosampler can be used to load a sample into the eluent.

Means for adding a flow of diluting solvent comprise an auxiliary pump 11 (also a high-pressure fluid pump) and the T-connector 6 disposed in the feed pipe 5 as shown. The auxiliary pump 11 adds a flow of diluting solvent to the flow of eluent from the pump 2 so that the flow of solvent into the column 1 comprises a mixture of the flows from both pumps. This permits the composition of eluent in the feed pipe 5 to be modified before the flow reaches the column 1. Thus, if the sample solvent comprises a high proportion of an organic solvent, the detrimental effect of a "slug" of such solvent on the recovery of analytes introduced into the column 1 can be mitigated by addition of an aqueous diluting solvent from the pump 11. This is especially valuable when the volume of the sample loop 4 is large in comparison with the volume of the column 1, as is typically the case with nanoflow columns designed for optimum efficiency at flow rates less than 1 µl/minute. In such a case, dilution with an aqueous dilution solvent as described may allow the use of a stronger sample solvent than would otherwise be possible without degrading the recovery of analytes. As shown below, this can improve the recovery of analytes present in a complex sample, especially in the case of a sample comprising a protein digest.

Eluate leaving the column 1 is passed to a suitable detector 12, for example a UV absorbance detector, an evaporative light scattering detector, or a mass spectrometer. An electrospray ionization or atmospheric pressure chemical ionization mass spectrometer is particularly suitable.

Figure 2:
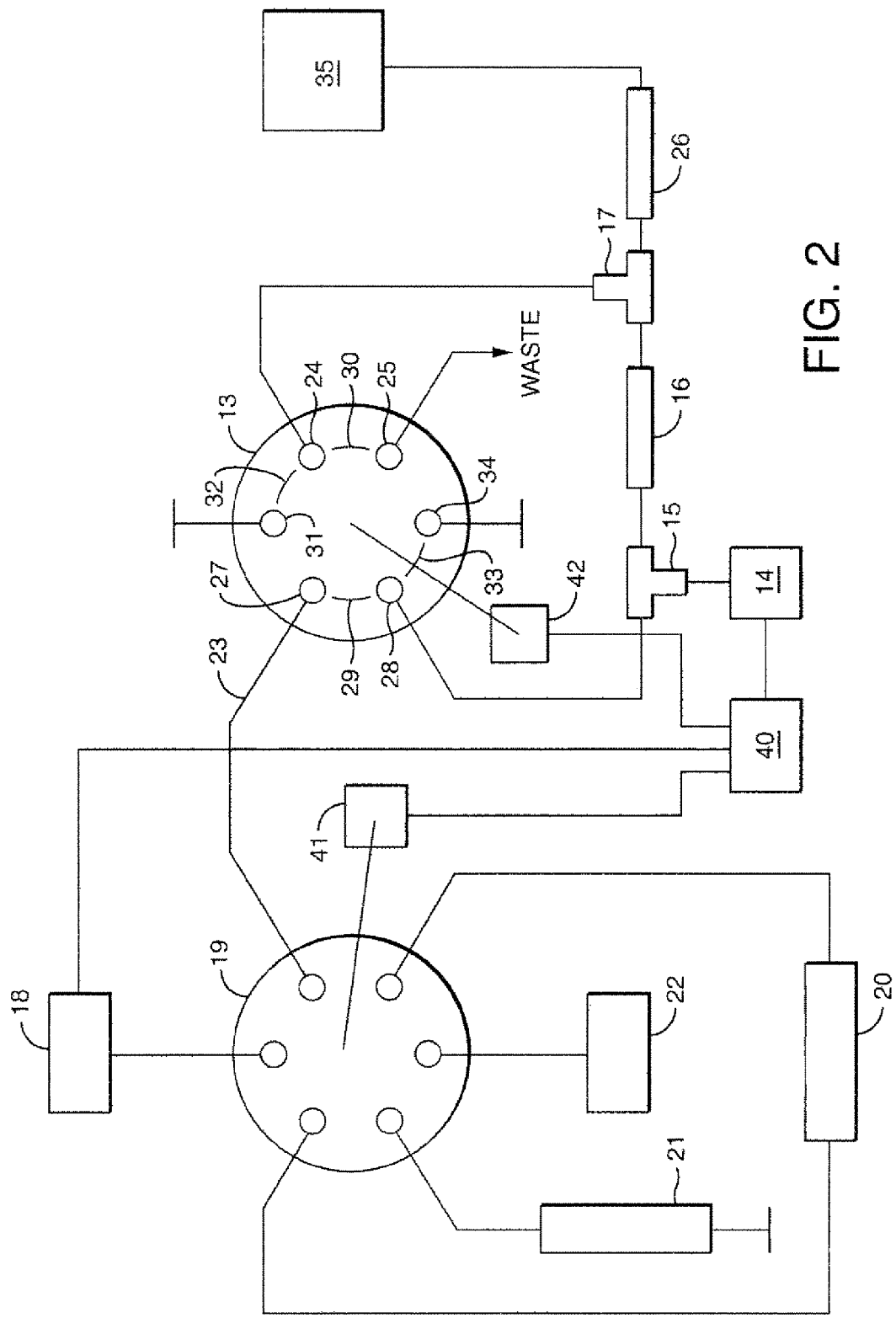
FIG. 2 is a schematic drawing of apparatus according to a second embodiment of the invention.

Especially in the case of chromatographic separation means comprising a nanoflow column operating at a flow rate of less than 1 µl/minute, advantage may result from the use of analyte trapping means in conjunction with the invention. A typical one-dimensional system is shown in FIG. 2. In this embodiment, means for delivering a flow of eluent comprises an auxiliary pump 18 (typically a high-pressure fluid pump). Means for introducing a sample comprising one or more analytes dissolved in a sample solvent may comprise a six-port sample valve 19 and a sample loop 20. In conjunction with a syringe 21 and a sample reservoir 22, this operates in a similar manner to valve 3 in the FIG. 1 embodiment to introduce a sample into a flow of eluent to produce a flow of a first analyte-bearing eluent in a feed pipe 23. This passes through ports 27 and 28 of a vent valve 13 and through a T-connector 15. Vent valve 13 is shown in the "trap" position wherein its ports are connected as indicated by the links 29 and 30. Means for adding a diluting solvent comprise a high-pressure binary fluid pump 14 connected to the T-connector 15 as shown so that a flow of diluted analyte bearing eluent into an analyte trapping means 16 may be generated. In use, at least some analytes comprised in a sample may be trapped on the analyte-trapping means 16 while the flow from the exit of the analyte-trapping means is directed to a T-connector 17. Conveniently, some of this flow may be directed to waste through ports 24 and 25 of valve 13. Port 25 is connected to a low-pressure discharge point so that the flow from the analyte-trapping means is routed through valve 13 rather than being forced through a chromatographic separation means 26 that is connected to the T-connector 17.

The process so far described therefore allows analytes comprised in a sample to be trapped in the analyte trapping means 16 while eluent from the pump 18 is discharged to waste. The flow rate of eluent from pump 18 is therefore independent of the flow rate required by the chromatographic separation means 26 and may therefore be relatively high (for example between 1 and 5 µl/minute), enabling a large volume sample loop 20 to be employed (for example, 2-10 µl). This allows a greater volume of sample to be injected than would be possible in the absence of the analyte trapping means, thereby reducing the detection limit of the analytes being separated. The addition of a diluting solvent, different from the eluent and/or the sample solvent, allows the use of a stronger sample solvent and/or eluent without causing premature release of analytes from the analyte trapping means, which has been found to improve analyte recovery, especially in the case of protein digest samples.

In order to carry out chromatographic separation of the analytes trapped in the analyte trapping means 16, chromatographic separation means 26, typically a reverse-phase C18 nanoflow column, are connected to the T-connector 17 as described. After analytes have been trapped in the analyte trapping means 16, valve 13 is changed from the "trap" position to the "run" position in which ports 27 and 31, and 25 and 34, are connected (as indicated by the links 32 and 33). Ports 24 and 28 are blanked off so that the flow from the analyte trapping means 16 is no longer vented to waste but instead is forced into the chromatographic separation means 26 and the flow from the pump 14 is directed into the analyte trapping means 16 and the chromatographic separation means 26. Chromatographic separation of these analytes may then be carried out using pump 14 to deliver a suitable eluting solvent. Typically, this will comprise a solvent gradient. Analytes eluting from the chromatographic separation means 26 are then passed to a detector 35, as in the embodiment illustrated in FIG. 1. In practice, the releasing solvent may conveniently comprise the solvent gradient itself, especially when the analyte trapping means and the chromatographic separation means comprise similar separation media.

In an example embodiment, the analyte trapping means 16 may comprise a short reverse-phase C18 column of relatively large diameter, capable of operation at a flow rate greater than 1 µl/minute and the chromatographic separation means 26 may comprise a nanoflow reverse-phase C18 column capable of operation at a flow rate less than 1 µl/minute.

Conveniently, valves 13 and 19 are fitted with actuators 42 and 41 respectively. These actuators, and the pumps 11 and 18 may be controlled by programmable control means 40 in order to perform the operations described above using parameters entered by the user that are appropriate to the separation being carried out. Programmable control means 40 may comprise any suitable device such as a computer, microprocessor, or programmable interface controller.

Figure 3:
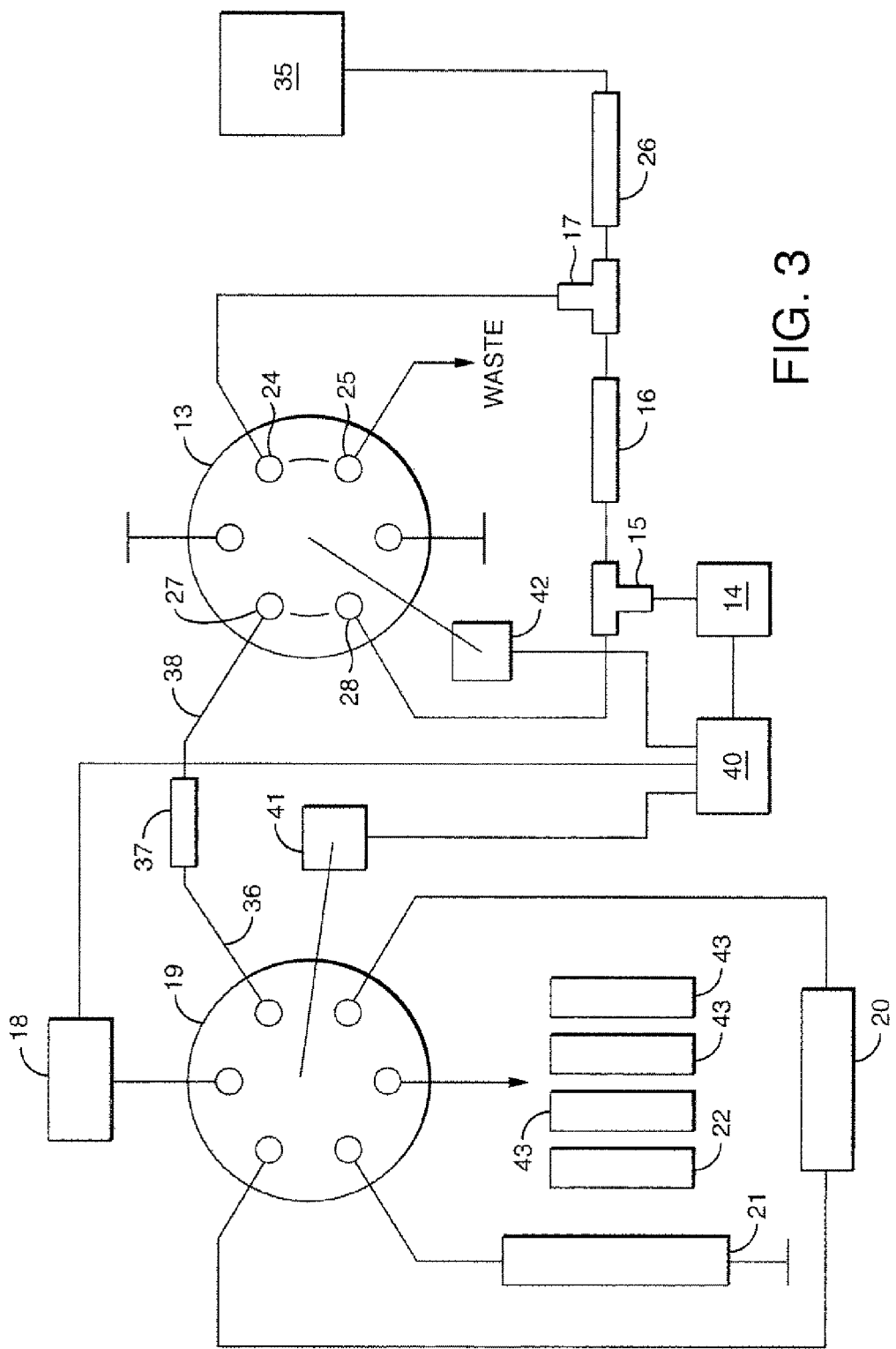
FIG. 3 is a schematic drawing of apparatus according to a third embodiment of the invention.
Figure 4A:
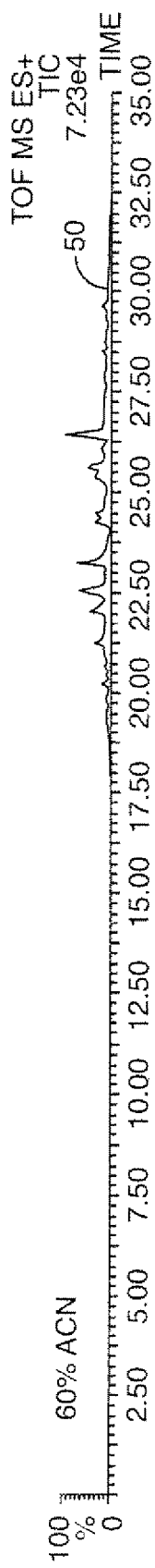
FIG. 4A-4G depict results obtained for the separation of a sample comprising a digest of a mixture of proteins using apparatus as shown in FIG. 3 as measured as total ion count by time of flight mass spectrometer acetylnitrate concentration is changed from 60 to 3%.
Figure 4B:
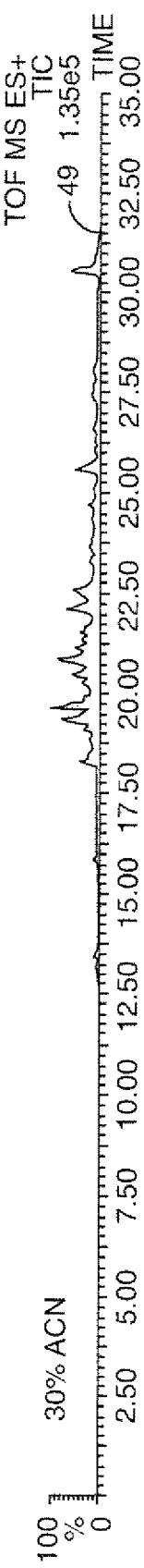
Figure 4C:
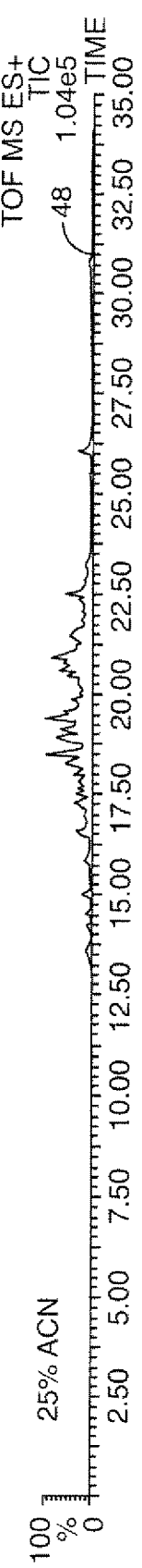
Figure 4D:
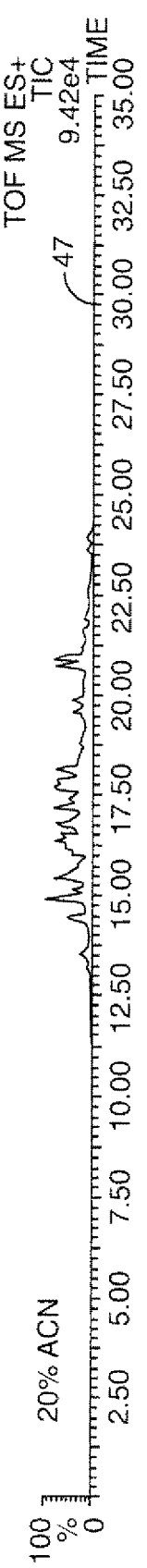
Figure 4E:
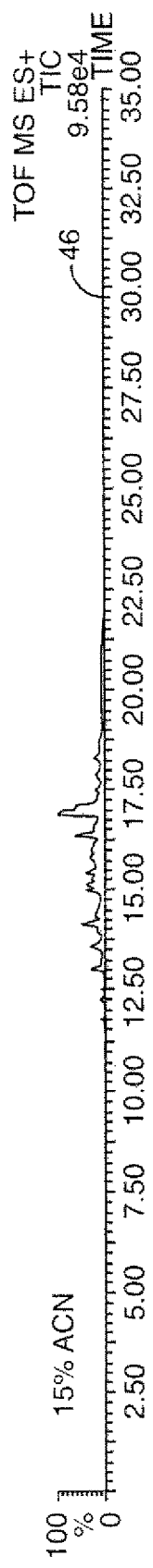
Figure 4F:
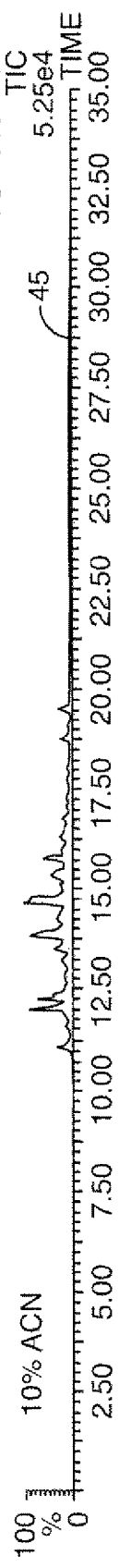
Figure 4G:
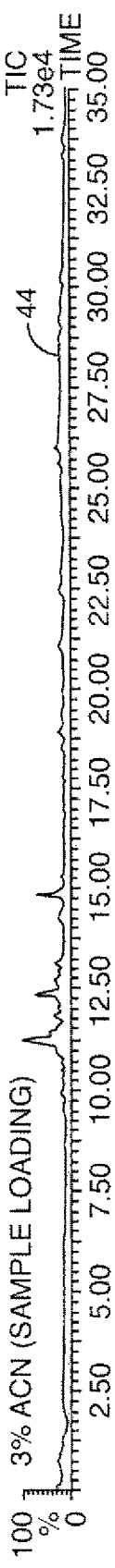

FIG. 3 illustrates an embodiment of the invention suitable for carrying out multi-dimensional chromatography. This embodiment provides means for introducing a sample into a flow of eluent delivered by an auxiliary pump 18, the means comprising a sample valve 19, sample loop 20, a sample reservoir 22 and syringe 21. These components operate in the same way as the similarly identified components in the embodiment shown in FIG. 2 to produce a flow of a first eluent bearing eluent in the pipe 36. This flow is passed to first chromatographic separation means 37, on which at least some analytes may be temporarily retained. A flow of intermediate eluent from the first chromatographic separation means 37 passes through pipe 38 to a vent valve 13 that operates in a similar manner to the similar valve shown in FIG. 2. With valve 13 in the "trap" position (shown in FIG. 3) the intermediate eluent from pipe 38 is routed via ports 27 and 28 to the T-connector 15 where a flow of diluting solvent from pump 14 is added. This generates a flow of diluted intermediate eluent into the analyte trapping means 16. While analytes are being trapped in the analyte trapping means, flow from its exit is routed to waste via the T-connector 17 and ports 24 and 25 of the valve 13. Analytes so trapped may then be released by operating valve 13 to the "run" position in which ports 24 and 28 are both blocked, so that a releasing solvent can be added from pump 14 into the T-connector 15, as in the case of the FIG. 2 embodiment. This generates a flow of a second analyte-bearing eluent that is passed to second chromatographic separation means 26, so that analytes released from the analyte trapping means 16 may be separated on the chromatographic separation means 26 and subsequently detected by a detector 35.

After this separation is complete, another batch of analytes may be released from the first chromatographic separation means 37, either by adjusting the composition of eluent form the pump 18 or by injecting a slug of a suitable solvent or other agent using valve 19, as described in more detail below. With valve 13 in the "trap" position, this batch of analytes may be trapped in the analyte trapping means and the process described above may be repeated to chromatographically separate these analytes on the second chromatographic separation means 26. If necessary, the entire process may be repeated, each time releasing another batch of analytes from the first chromatographic separation means 37 and subsequently separating them on the second chromatographic separation means 26.

Conveniently, programmable control means 40 are provided to control valve 19 via actuator 41, valve 13 via actuator 42, and pumps 18 and 14, as in the case of the embodiment shown in FIG. 2. Such control means may typically also control the composition of the solvents supplied by pumps 14 and 18.

It will be appreciated that multidimensional chromatographic apparatus as described can be configured and operated in a number of different ways, all of which are within the scope of the invention. Any suitable chromatographic columns can be used or the first and second chromatographic separation means 37 and 26. The analyte trapping means 16 may conveniently comprise media having similar separation properties to that used in the second chromatographic separation means, but this is not essential. It is required only that at least some analytes present in a sample can be trapped and subsequently released by a suitable releasing solvent, which may or may not be the solvent used to elute analytes from the second chromatographic separation means.

In a particular embodiment of a multidimensional chromatography system as described the first and second chromatographic separation means and the analyte trapping media may all comprise reverse-phase separation media. The first chromatographic separation means and the analyte trapping means comprise columns capable of operation at higher flow rates than the second chromatographic separation means. A specific example of such a separation is given below. Pump 14 may comprise a binary gradient liquid chromatography pump, for example a nanoAQUITY™ pump available from Waters Corporation, Milford, Mass. This pump can be used to provide a solvent gradient of gradually increasing strength (that is, an increasing proportion of organic solvent) into the T-connector 15 which serves both as a releasing solvent (to release analytes from the analyte trapping means 16) and as a gradient elution solvent to separate analytes on the second chromatographic separation means. Pump 14 may also be used to deliver a flow of diluting solvent (in this case, typically comprising a high proportion of an aqueous solvent) while analytes are being trapped in the analyte trapping means 16.

It will be appreciated that in an RP/RP separation, the addition of an aqueous diluting solvent reduces the strength of the solvent in the first analyte bearing eluent that enters the analyte-trapping means, preventing premature release of the analytes that might otherwise occur if the eluent is too strong. This greatly reduces restrictions on the composition of the eluent used to release analytes from the first chromatographic separation means and improves the performance and versatility of the RP/RP method.

Any suitable high-pressure liquid chromatography pump may be used for pump 18. This need only be capable of generating a solvent gradient if it is used to release analytes by changing the composition of the eluent used to transfer them to the first chromatographic separation means. Another method of releasing batches of analytes from the first chromatographic separation means may involve the injection of slugs of a suitable solvent by means of valve 19. In such a case, sample loop 20 is first filled with a suitable solvent from one of a set or reservoirs 43 using the syringe 21, as though it was a sample, with valve 19 in the "load" position. When it is desired to release a batch of analytes, valve 19 is turned to the "run" position so that the eluent from pump 18 carries the solvent from the loop 20 in the form of a slug, which, when it reaches the first chromatographic separation means causes the release of a batch of analytes. In the case of an RP/RP separation, reservoirs 43 may contain a series of solvents of gradually increasing organic concentrations, each capable of releasing a different batch of analytes from the first chromatographic separation means. An autosampler is particularly useful in such a method.

The sample introduction means may comprise a six-port valve 19 and a sample loop 20, as illustrated, or may comprise an autosampler capable of introducing a sample into a flow of eluent from any one of a number of reservoirs 22, 43. Conveniently, this will also be controlled by the programmable control means 40.

In another specific embodiment of a multidimensional chromatography system as described, the first and second chromatographic separation means may comprise different separation media. A typical example might be the use of an SCX (strong cation exchange) column for the first chromatographic separation means and a nanoflow reverse-phase column for the second chromatographic separation means. In such a SCX/RP system, batches of analytes trapped on the SCX column may conveniently be released by the injection of "salt plugs" of gradually increasing concentration. A certain organic concentration may be required in the plugs to eliminate the unwanted hydrophobic interaction between the analytes and the SCX media. Addition of an aqueous diluting solvent as described can reduce the organic concentration and help analytes eluting from the SCX column be retained onto the analyte trapping means 16.

Both SCX/RP and RP/RP two-dimensional separations are especially useful when the detector 35 comprises a mass spectrometer, for example a tandem time-of-flight mass spectrometer equipped with an electrospray, APCI (atmospheric pressure chemical ionization), or APPI (atmospheric pressure photoionization) source. A suitable spectrometer may comprise the Q-TOF™ mass spectrometer available from Waters Corporation, Milford, Mass. SCX/RP and RP/RP systems with mass spectrometric detection as described above are especially valuable for the analysis of peptide digests from a mixture of proteins.

FIG. 4 shows results obtained in respect of a RP/RP separation as described above, using apparatus as shown in FIG. 3. The first chromatographic separation means 37 comprised an XBRIDGE™ C18 100 μm×100 mm chromatographic column, and the analyte trapping means 16 comprised a SYMMETRY™ C18 180 μm×20 mm chromatographic column, both available from Waters Corporation, Milford, Mass. The second chromatographic separation means 26 comprised an AQUITY™ BEH (bridged ethyl hydride) reverse-phase nanoflow 75 μm×100 mm column (Waters Corporation). Pumps 14 and 18, valves 13 and 19 and their associated actuators 41 and 42, and the programmable control means 40 were comprised in a Waters Corporation nanoAQUITY™ HPLC system, modified as shown in FIG. 3. The first dimension separation was carried out using a water/acetonitrile solvent mixture buffered to pH 10.0 with 20 mM ammonium formate and the second dimension separation was carried out using a water/acetonitrile solvent buffered to pH 2.6 by 0.1% formic acid. The detector 35 comprised a Waters MS Technologies Q-TOF mass spectrometer operated in the positive ion electrospray mode. For the purposes of this example only the total ion current was measured.

A sample comprising 100 fmol. of a tryptic digest of 5 proteins dissolved in a sample solvent comprising 3% acetonitrile and 97% water (buffered at pH 10.0 with 20 mM ammonium formate) was prepared and introduced into the sample loop 20 (2 μl volume) from the reservoir 22. This was admitted to the first chromatographic separation means using eluent of the same composition as the sample solvent from the pump 18 at a flow rate of 1 μl/minute. A diluting solvent comprising 100% water buffered by 0.1% formic acid was simultaneously introduced at a flow rate of 10 μl/minute using pump 14 to mix with the first analyte bearing eluent in the T-connector 15, thereby reducing the pH and the concentration of acetonitrile in the eluent entering the analyte-trapping means 16. Valve 13 was set to the "trap" position in which ports 24 and 25 were connected to direct eluent from the analyte trapping means 16 to waste. This resulted in analytes not retained on the first chromatographic separation means being trapped in the analyte-trapping means. Valve 13 was then turned to the "run" position to discontinue the flow of eluent from the first chromatographic separation means into the analyte trapping means and causing the flow from the analyte trapping means to enter the second chromatographic separation means. Pump 14 was then caused to generate a flow of a releasing solvent comprising a solvent gradient of 3% to 50% acetonitrile in water, buffered at pH 2.6 by 0.1% formic acid, over a period of 30 minutes. This released analytes trapped on the analyte trapping means and separated them in the second chromatographic separation means. The total ion chromatogram produced by the mass spectrometer used as detector 37 is shown at 44 in FIG. 4.

Next, valve 13 was returned to the "trap" position and pump 18 readjusted to provide a flow of 100% water buffered by 0.1% formic acid at 10 μl/min as a diluting solvent. A solvent plug comprising 2 μl of 10% acetonitrile and 90% water from one of the reservoirs 43 at 1 μl/min was injected into the eluent from pump 18. The passage of this solvent plug through the first chromatographic separation means eluted a second batch of analytes that were then trapped in the analyte-trapping means. The 11-fold organic dilution (from 10% to less than 1% acetonitrile) ensured that this batch of analytes remained in the analyte-trapping means, despite the increased concentration of acetonitrile in the eluent. Valve 13 was then returned to the "run" position and pump 14 readjusted to supply the releasing solvent gradient, as above. This resulted in separation of the second batch of analytes and produced the total ion chromatogram shown at 45 in FIG. 4.

Figure 5C:
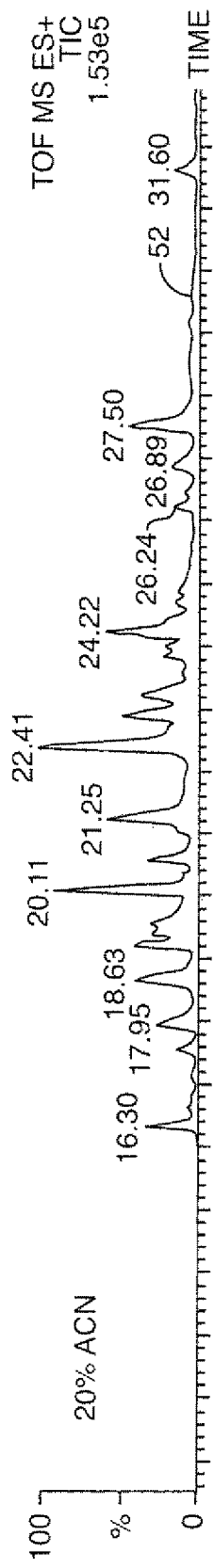
Figure 5D:
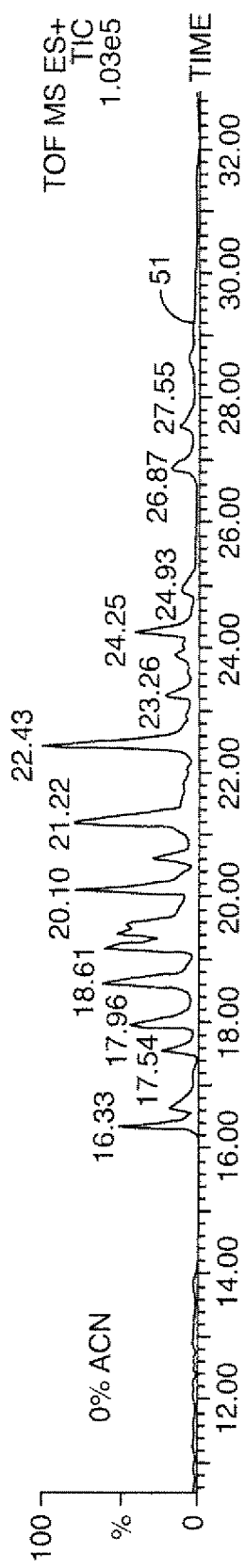

Next, the whole process was repeated several times, injecting in turn solvent plugs comprising 15%, 20%, 25%, 30% and 60% acetonitrile. The corresponding total ion chromatograms are shown at 46-50 in FIG. 4. FIG. 5 is an example of how the recovery of peptides in a sample may be improved by the use of a sample solvent comprising a high proportion of an organic solvent, made possible by the use of on-line dilution as described. It shows four total ion chromatograms obtained for four samples of an enolase digest obtained by reverse-phase separation using the apparatus of FIG. 2. The chromatographic separation means 26 comprised an ATLANTIS™ dC18 75 μm×100 mm column and the analyte-trapping means 16 comprised a SYMMETRY™ C18 250 μm×10 mm column (both available from Waters Corporation, Milford, Mass.). The detector 35 comprised a Waters MS Technologies Q-TOF mass spectrometer operated in the positive ion electrospray mode. The mobile phase employed comprised a solvent gradient from 3% acetonitrile/97% water to 50% acetonitrile/50% water over 30 minutes, buffered with 0.1% formic acid, supplied from pump 14 at a flow rate of 250 μl/minute. Different sample solvents were used to prepare the four samples. Total ion chromatogram 51 was obtained from a sample dissolved in a sample solvent comprising 100% water and using a sample loading flow rate (from pump 18) of 3.5 μl/minute. Chromatogram 52 was obtained from the same sample dissolved in a sample solvent comprising 20% acetonitrile/80% water, loaded at a flow rate of 3.5 μl/minute.

Chromatograms 53 and 54 were obtained from solutions made up in 40% acetonitrile/60% water, loaded at 1.56 μl/minute and 60% acetonitrile/40% water loaded at 1.0 μl/minute, respectively. In each case, during trapping of analytes in the analyte-trapping means, pump 14 was used to add a diluting solvent comprising 100% water buffered by 0.1% formic acid at a flow rate of 14 μl/minute.

Comparison of chromatograms 51-54 clearly shows that recovery of peptides comprised in the digest increases with the increasing concentration of acetonitrile in the sample solvent. In particular, the increasing size of the peak of retention time 31.6 minutes, completely absent in chromatogram 51 and maximum in chromatogram 54, may be noted. Although the cause of this is not fully understood, it is clear that maximum recovery is possible only when a high concentration of acetonitrile is present in the sample solvent, and this can only be used when an aqueous diluting solvent is added during the analyte trapping phase. Without it, the analytes would not be trapped in the analyte-trapping means.

Figure 6A:
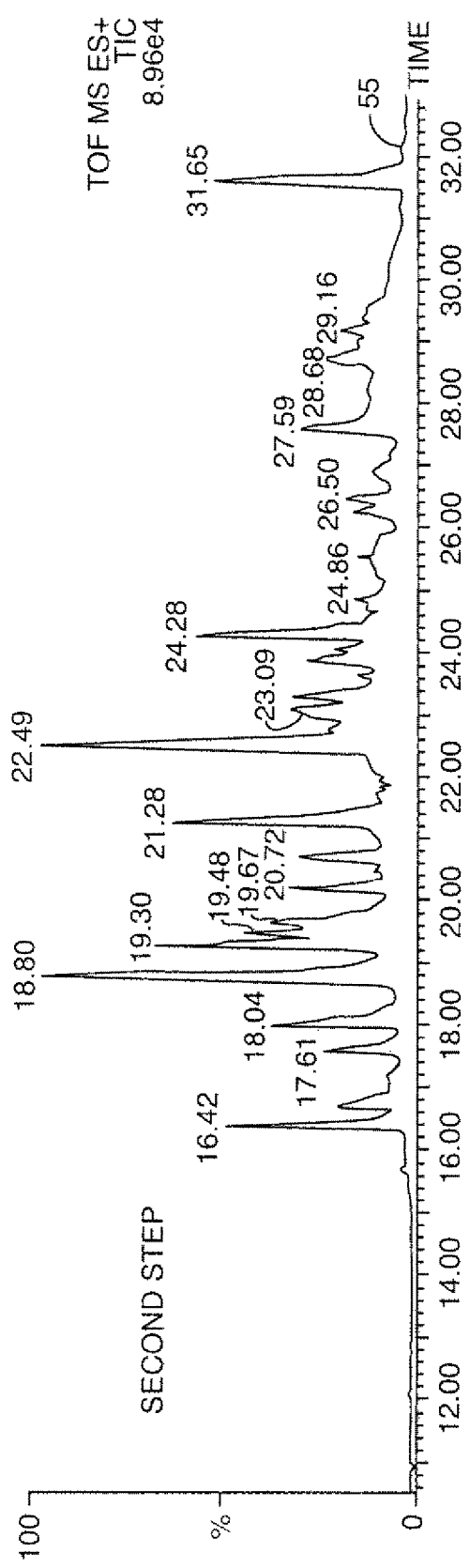
FIGS. 6A and 6B depict results obtained for the separation of a sample of an enolase digest obtained using apparatus as shown in FIG. 3 as measured as total ion count by time of flight mass spectrometer as acetylnitrate concentration is changed from 3% to 50%.
Figure 6B:
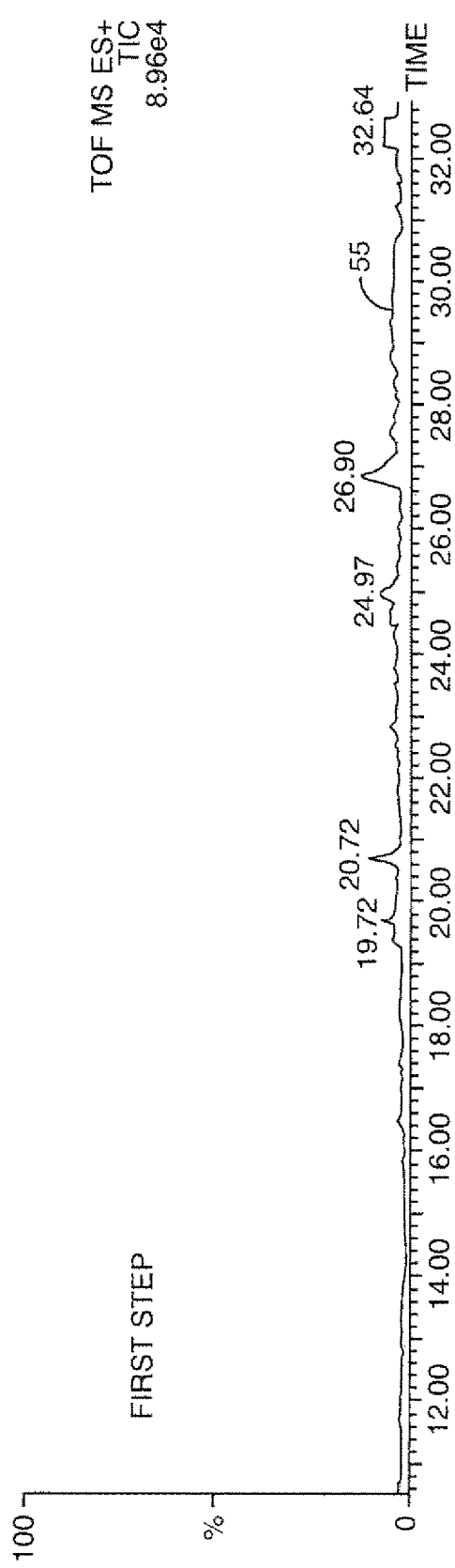

FIG. 6 is a simple example of a two-dimensional separation using an SCX column in the first dimension and a RP column in the second dimension. The two chromatograms 55 and 56 were obtained using a Waters Q-TOF mass spectrometer as described above as the detector. Apparatus according to FIG. 3 was employed, using a Whatman 180 μm×2.4 cm 5 μm PARTISHERE™ SCX column for the first chromatographic separation means and a Waters ATLANTIS™ dC18 75 μm×100 mm column for the second chromatographic separation means. A Waters SYMMETRY™ C18 250 μm×10 mm column was used for the analyte-trapping means. The sample comprised the same enolase digest used to obtain the results show in FIG. 5, dissolve in a sample solvent comprising 40% acetonitrile/60% water. An eluent comprising 97% water, 3% acetonitrile buffered by 0.1% formic acid was supplied by pump 18 at a flow rate of 1.56 μl/minute for 4 minutes to load the analytes in the sample on the SCX column. Under these conditions, some peptides were not retained on the SCX column but were immediately passed to the analyte-trapping means while a diluting solvent comprising 97% water/3% acetonitrile buffered by 0.1% formic acid was added at a flow rate of 14 μl/minute by pump 14. After the trapping phase was complete, the trapped analytes were released from the analyte trapping means by a solvent gradient starting at 3% acetonitrile/97% water rising to 50% acetonitrile/50% water in 30 minutes, delivered by pump 14 at a flow rate of 250 μl/minute. This gradient subsequently resulted in separation of the released analytes on the RP column to give chromatogram 55.

A second batch of peptides was then released from the SCX column by injecting a salt plug from one of the reservoirs 43 into the eluent from pump 18. The salt plug comprised a 400 mM solution of ammonium formate in a 40% acetonitrile/60% water mixture. The analytes released by this salt plug were trapped on the analyte trapping means while the diluting solvent was being added, as described above. After trapping, the released analytes were separated on the RP column as described above, to yield chromatogram 56. It is again noted that the use of an eluent comprising 40% acetonitrile for the salt plug is made possible only by the addition of diluting solvent as described.

The invention is not limited to the use or RP/RP or SCX/RP separations. It is equally applicable to multidimensional separations, or trapped single dimensional separations, especially those using low-flow rate nanoflow columns, using normal phase separation media. In such cases, the strong solvent would comprise aqueous solutions, and the diluting solvent would typically comprise a solvent having a high concentration of an organic solvent.

The invention claimed is:

1. A method of separating analytes in a sample that comprises one or more analytes dissolved in a sample solvent, said method comprising the steps of introducing an aliquot of a said sample into a flow of an eluent to form of a first analyte-bearing eluent having a first eluent flow rate, adding to said flow of first analyte-bearing eluent a flow of a diluting solvent, different from said sample solvent, to form a flow of a diluted analyte-bearing eluent, passing at least some of said flow of diluted analyte-bearing eluent into a reverse-phase column to trap therein at least one of said analytes, passing at least a releasing solvent into said reverse phase column to release at least one analyte trapped therein and to form a flow of a second analyte-bearing eluent having a second eluent flow rate, and passing at least some of said flow of second analyte-bearing eluent into chromatographic separation means to separate said one or more analytes wherein the first eluent flow rate is independent of the second eluent flow rate and the first eluent flow rate is 1 to 5 times the second eluent flow rate.

2. The method as claimed in claim 1 further comprising changing the composition with time of at least one of said eluent, said diluting solvent and said releasing solvent so that a gradient elution takes place on said chromatographic separation means.

3. The method as claimed in claim 1 wherein said sample solvent comprises 40 to 60 percent organic solvent and said diluting solvent comprises 97 percent water.

4. The method as claimed in claim 1 further comprising diverting to waste at least some of the flow from said reverse-phase column prior to the introduction of said releasing solvent.

5. The method as claimed in claim 1 wherein said releasing solvent is obtained by changing the composition of one or both of said eluent and said diluting solvent so that at least some analytes are released from said reverse-phase column.

6. A method of separating analytes in a sample that comprises one or more analytes dissolved in a sample solvent, said method comprising introducing an aliquot of a said sample into a flow of an eluent to form a flow of a first analyte-bearing eluent having a first eluent flow rate, passing at least some of said flow of analyte-bearing eluent through first chromatographic separation means to form a flow of an intermediate eluate, adding a diluting solvent to at least some of said flow of intermediate eluate to form a flow of a diluted intermediate eluate, and passing at least some of said diluted intermediate eluate onto a reverse-phase column to trap said one or more analytes, wherein a releasing solvent is passed into reverse-phase column to release at least one analyte trapped therein and to form a flow of a second eluent having a second eluent flow rate wherein the first eluent flow rate is independent of the second eluent flow rate and the first eluent flow rate is 1 to 5 times the second eluent flow rate and the flow of the second eluent from the reverse-phase column comprises a waste portion and an analytical portion, said waste portion diverted to waste and said analytical portion directed so that at least one of said analytes is passed into a second chromatographic separation means to separate said one or more analytes.

7. The method as claimed in claim 6 wherein said diluting solvent differs in composition from said eluent.

8. The method as claimed in claim 6 further comprising selecting said eluent and said diluting solvent so that said analytes undergo different separations on said first chromatographic separation means and said second chromatographic separation means.

9. The method as claimed in claim 6 further comprising selecting said first and said second chromatographic separation means so that according to their different physiochemical properties, at least one analyte will be retained on one of said first and second chromatographic separation means and will not be retained or separated on remaining chromatographic separation means.

10. The method as claimed in claim 6 further comprising changing with time the composition of at least one of said first analyte-bearing eluent and said diluting solvent so that gradient elution may take place on at least one of said first or said second chromatographic separation means.

11. The method as claimed in claim 10 further comprising introducing into said flow of the first analyte-bearing eluent at least one predetermined quantity of a different solvent at predetermined time intervals in order to change its composition.

12. A method of separating analytes in a sample that comprises one or more analytes dissolved in a sample solvent, said method comprising introducing an aliquot of a said sample into an eluent to form a first analyte-bearing eluent having a first eluent flow rate, passing at least some of said first analyte-bearing eluent through first chromatographic separation means to form a flow of an intermediate eluate, adding to said flow of intermediate eluate a diluting solvent to form a flow of a diluted intermediate eluate, passing at least some of said diluted intermediate eluate through a reverse-phase column to trap at least one of said analytes, passing at least a releasing solvent into said reverse-phase column to release at least one analyte trapped therein and to form a flow of a second analyte-bearing eluent having a second eluent flow rate, and passing at least some of said second analyte-bearing eluent into second chromatographic separation means wherein the first eluent flow rate is independent of the second eluent flow rate and the first eluent flow rate is 1 to 5 times the second eluent flow rate.

13. The method as claimed in claim 12 further comprising changing with time the composition of said eluent in order to carry out a gradient elution on said first chromatographic separation means.

14. The method as claimed in claim 12 further comprising changing with time the composition of at least one of said eluent, said diluting solvent and said releasing solvent in order to carry out a gradient elution on said second chromatographic separation means.

15. The method as claimed in claim 14 further comprising carrying out a reverse phase separation on said first chromatographic separation means using a gradient elution with an increasing proportion of organic solvent.

16. The method as claimed in claim 15 wherein said diluting solvent comprises a high proportion of an aqueous solvent.

17. The method as claimed in claim 12 further comprising diverting to waste at least some of the flow from said reverse-phase column while said intermediate eluate flows into said analyte trapping means.

18. The method as claimed in claim 17 further comprising passing said first analyte-bearing analyte into said first chromatographic separation means in order to trap analytes therein and simultaneously passing at least one of said releasing solvent and said diluting solvent into said second chromatographic separation means to separate analytes already present therein.

19. The method as claimed in claim 12 further comprising passing said first analyte-bearing analyte into said first chromatographic separation means in order to trap analytes therein and simultaneously passing at least one of said releasing solvent and said diluting solvent into said second chromatographic separation means to separate analytes already present therein.

20. The method as claimed in claim 12 further comprising generating said releasing solvent by introducing an aliquots of a solvent different from said eluent into said eluent such that on passing through said first chromatographic separation means into said intermediate eluate, said aliquot of different solvent releases at least some analytes from said reverse-phase column to form said second analyte-bearing eluent.

21. The method as claimed in claim 20 further comprising consecutively introducing aliquots of said different solvent into said eluent such that each said aliquot generates a releasing solvent of different strength, thereby consecutively releasing different ones of said analytes from said analyte trapping means to form said second analyte-bearing eluent.

22. The method as claimed in claim 21 wherein the reduction in the recovery of analytes from said second chromatographic separation means which might result from the presence of a high proportion of organic solvent in said intermediate eluate is minimized by the addition of a said diluting solvent comprising a high proportion of aqueous solvent.

23. The method as claimed in claim 20 wherein the reduction in the recovery of analytes from said second chromatographic separation means which might result from the presence of a high proportion of organic solvent in said intermediate eluate is minimized by the addition of a said diluting solvent comprising a high proportion of aqueous solvent.

24. The method as claimed in claim 12 further comprising changing the composition of said eluent with time so that on passing through said first chromatographic separation means into said intermediate eluate, it generates a releasing solvent of increasing strength, thereby causing progressive release of different ones of said analytes from said reverse-phase column into said second analyte-bearing eluent.

25. The method as claimed in claim 12 wherein the reduction in the recovery of analytes from said second chromatographic separation means which might result from the presence of a high proportion of organic solvent in said intermediate eluate is minimized by the addition of a said diluting solvent comprising a high proportion of aqueous solvent.

26. Apparatus for separating analytes in a sample that comprises one or more analytes dissolved in a sample solvent, said apparatus comprising means for delivering a flow of an eluent, means for introducing said sample into said flow of eluent to form a flow of a first analyte-bearing eluent having a first eluent flow rate, means for adding to said flow of first analyte-bearing eluent a flow of a diluting solvent, different from said sample solvent, to form a flow of diluted analyte-bearing eluent, a reverse-phase column disposed to receive at least some of said flow of diluted analyte-bearing eluent to trap therein at least one of said analytes, means for introducing at least a releasing solvent into said reverse-phase column to release at least one of the analytes trapped therein to form a flow of a second analyte-bearing eluent having a second eluent flow rate, and chromatographic separation means disposed to receive at least some of said flow of second analyte-bearing eluent, and chromatographic separation means disposed to receive at least some of said flow of diluted analyte-bearing eluent to separate said one or more analytes wherein the first eluent flow rate is independent of the second eluent flow rate and the first eluent flow rate is 1 to 5 times the second eluent flow rate.

27. Apparatus as claimed in claim 26 further comprising programmable control means for controlling said means for delivering a flow of eluent, said means for introducing a sample, said means for adding a diluting solvent and said means for introducing at least a releasing solvent.

28. Apparatus as claimed in claim 27 wherein said means for delivering an eluent comprises a binary fluid pump capable of delivering fluid through said analyte trapping means to said chromatographic separation means to allow a chromatographic separation of at least some of said analytes to be carried out, and said programmable control means is programmed to cause said means for delivering said flow of diluting solvent to discontinue the addition of a diluting solvent after at least some analytes have been trapped in said reverse-phase column.

29. Apparatus as claimed in claim 27 wherein said means for introducing at least a releasing solvent comprises a binary high-pressure fluid pump capable of providing a flow of solvent whose composition changes with time, and wherein said programmable control means is programmed to cause said binary high-pressure pump to generate a flow of releasing solvent whose composition changes with time so that said releasing solvent may elute analytes from said chromatographic separation means as well as release analytes from said reverse-phase column.

30. Apparatus as claimed in claim 29 wherein said means for adding a flow of diluting solvent comprises said binary high-pressure fluid pump, and said programmable control means is further programmed to provide said flow of diluting solvent while analytes are being trapped in said reverse-phase column and to provide said flow of releasing solvent when analytes are being released from reverse-phase column and passed to said chromatographic separation means.

31. Apparatus as claimed in claim 26 further comprising means for diverting to waste at least some of the eluate from reverse-phase column while analytes are being trapped therein.

32. Apparatus as claimed in claim 26 wherein said chromatographic separation means comprises a nanoflow chromatographic column capable of optimum performance at a flow rate of less than 1 µl/minute and said reverse-phase column is capable of trapping analytes at a flow rate greater than 1 µl/minute.

33. Apparatus as claimed in claim 26 wherein said means for introducing analytes dissolved in a sample solvent comprises valve means configured to introduce into said flow of eluent a fixed volume of a said sample solvent from a loop.

34. Apparatus for separating analytes in a sample that comprises one or more analytes dissolved in a sample solvent, said apparatus comprising means for delivering a flow of an eluent, means for introducing said sample into said flow of eluent to form a flow of a first analyte-bearing eluent having a first eluent flow rate, first chromatographic separation means disposed to receive at least some of said flow of first analyte-bearing eluent to form a flow of an intermediate eluate, means for adding to said flow of intermediate eluate a flow of a diluting solvent to form a flow of diluted intermediate eluate, a reverse-phase column disposed to receive at least some of said flow of diluted intermediate eluate to trap therein at least one of said analytes, means for introducing at least a releasing solvent into said reverse-phase column to release at least one of the analytes trapped therein and to form a flow of a second analyte-bearing eluent having a second eluent flow rate, and second chromatographic separation means disposed to receive at least some of said flow of second analyte-bearing eluent to separate said one or more analytes wherein the first eluent flow rate is independent of the second eluent flow rate and the first eluent flow rate is 1 to 5 times the second eluent flow rate.

35. Apparatus as claimed in claim 34 further comprising programmable control means for controlling said means for delivering a flow of eluent, said means for introducing a sample, said means for adding a diluting solvent and said means for introducing at least a releasing solvent.

36. Apparatus as claimed in claim 35 wherein said means for delivering a flow of eluent comprises an eluent pump, and said programmable control means is programmed to cause said eluent pump to generate a flow of eluent having a composition such that at least some analytes comprised in a said sample introduced into said flow of eluent undergo separation on said first chromatographic separation means before passing into said intermediate eluate.

37. Apparatus as claimed in claim 35 wherein said programmable control means is programmed:
a) to cause said means for delivering a flow of eluent to deliver eluent of a first strength to said first chromatographic separation means so that a first group of analytes present in a said sample is eluted from said first chromatographic separation means and trapped in said reverse-phase column;
b) to cause said means for adding a flow of diluting solvent to add a diluting solvent while said first group of analytes are being trapped in said reverse-phase column;
c) to cause said means for introducing a releasing solvent to introduce a releasing solvent into said reverse-phase column once said first group of analytes have been trapped therein, and to separate at least some of said first group of analytes on said second chromatographic separation means;
d) after at least some of said first group of analytes have passed through said second chromatographic separation means, to cause said means for delivering a flow of eluent to deliver eluent of a second strength so that a second group of analytes previously present in said first chromatographic separation means is eluted from said first chromatographic separation means and trapped in said reverse-phase column;
e) to cause said means for adding a flow of diluting solvent to add a diluting solvent while said second group of analytes are being trapped in said reverse-phase column; and
f) to cause said means for introducing a releasing solvent to introduce a releasing solvent into said reverse-phase column once said second group of analytes have been trapped therein, and to separate at least some of said second group of analytes on said second chromatographic separation means.

38. Apparatus as claimed in claim 35 wherein said programmable control means is programmed:
a) to cause said means for delivering a flow of eluent to deliver eluent of a predetermined strength to said first chromatographic separation means;
b) while the eluate from said reverse-phase column is diverted to waste, to cause said means for introducing a sample to introduce a sample comprising at least a first and a second group of analytes into said flow of eluent so that said first and said second groups of analytes are separated from one another on said first chromatographic separation means and only said first group of analytes is eluted and trapped in said reverse-phase column;

c) to cause said means for adding a flow of diluting solvent to add a diluting solvent while said first group of analytes are being trapped in said reverse-phase column;
d) to cause said means for introducing a releasing solvent to introduce a releasing solvent into said reverse-phase column once said first group of analytes have been trapped therein and to separate at least some of said second group of analytes on said second chromatographic separation means;
e) after at least some of said first group of analytes have passed through said second chromatographic separation means and while the eluate from said analyte trapping means is diverted to waste, to cause said means for introducing a sample to introduce into said flow of eluent an aliquot of a different solvent to increase the strength of said eluent so that second group of analytes is eluted from said first chromatographic separation means and trapped in said reverse-phase column;
f) to cause said means for adding a flow of diluting solvent to add a diluting solvent while said second group of analytes are being trapped in said reverse-phase column; and
g) to cause said means for introducing a releasing solvent to introduce a releasing solvent into said reverse-phase column once said second group of analytes have been trapped therein, and to separate at least some of said second group of analytes on said second chromatographic separation means.

39. Apparatus as claimed in claim 35 wherein said means for adding a flow of diluting solvent comprises a binary high-pressure fluid pump, and wherein said programmable control means is programmed to cause said binary high-pressure pump to provide said flow of diluting solvent while analytes are being trapped in said reverse-phase column and to provide said flow of releasing solvent when analytes are being released from said reverse-phase column and passed to said second chromatographic separation means.

40. Apparatus as claimed in claim 39 wherein said means for introducing at least a releasing solvent comprises said binary high-pressure fluid pump and wherein said programmable control means is further programmed to generate a flow of releasing solvent whose composition changes with time so that said releasing solvent may also be used to separate analytes on said second chromatographic separation means as well as to release analytes from said reverse-phase column.

41. Apparatus as claimed in claim 40 wherein said means for delivering a flow of eluent comprises an eluent pump, and said programmable control means is programmed to cause said eluent pump to generate a flow of eluent having a composition such that at least some analytes comprised in a said sample introduced into said flow of eluent undergo separation on said first chromatographic separation means before passing into said intermediate eluate.

42. Apparatus as claimed in claim 41 wherein said programmable control means is programmed:
a) to cause said eluent pump deliver eluent of a first strength to said first chromatographic separation means so that a first group of analytes present in a said sample is eluted from said first chromatographic separation means and trapped in said reverse-phase column while the eluate from said reverse-phase column is diverted to waste;
b) to cause said binary high-pressure fluid pump to add a diluting solvent while said first group of analytes are being trapped in said reverse-phase column;
c) after said first group of analytes have been trapped in said reverse-phase column, to cause said binary high-pressure pump to introduce a releasing solvent into said reverse-phase column while the eluate from said reverse-phase column is directed to said second chromatographic separation means;
d) to cause said binary high-pressure pump to change the composition of said releasing solvent to separate at least some of said first group of analytes on said second chromatographic separation means;
e) after at least some of said first group of analytes have passed through said second chromatographic separation means, to cause said eluent pump to deliver eluent of a second strength so that a second group of analytes previously present in said first chromatographic separation means is eluted from said first chromatographic separation means and trapped in said reverse-phase column while the eluate from said reverse-phase column is diverted to waste;
f) to cause said binary high-pressure fluid pump to add a diluting solvent while said second group of analytes are being trapped in said reverse-phase column;
g) after said second group of analytes have been trapped in said reverse-phase column, to cause said binary high-pressure pump to introduce a releasing solvent into said reverse-phase column while the eluate from said reverse-phase column is directed to said second chromatographic separation means; and
h) to cause said binary high-pressure pump to change the composition of said releasing solvent to separate at least some of said second group of analytes on said second chromatographic separation means.

43. Apparatus as claimed in claim 41 wherein said programmable control means is programmed:
a) to cause said eluent pump deliver eluent of a predetermined strength to said first chromatographic separation means;
b) while the eluate from said reverse-phase column is diverted to waste, to cause said means for introducing a sample to introduce a sample comprising at least a first and a second group of analytes into said flow of eluent so that said first and said second groups of analytes is separated from one another on said first chromatographic separation means and only said first group of analytes is eluted and trapped in said reverse-phase column;
c) to cause said binary high-pressure fluid pump to add a diluting solvent while said first group of analytes are being trapped in said reverse-phase column;
d) after said first group of analytes have been trapped in said reverse-phase column, to cause said binary high-pressure pump to introduce a releasing solvent into said reverse-phase column while the eluate from said reverse-phase column is directed to said second chromatographic separation means;
e) to cause said binary high-pressure pump to change the composition of said releasing solvent to separate at least some of said first group of analytes on said second chromatographic separation means;
f) after at least some of said first group of analytes have passed through said second chromatographic separation means and while the eluate from said reverse-phase column is diverted to waste, to cause said means for introducing a sample to introduce into said flow of eluent an aliquot of a different solvent to increase the strength of said eluent so that second group of analytes is eluted from said first chromatographic separation means and trapped in said reverse-phase column;

g) to cause said binary high-pressure fluid pump to add a diluting solvent while said second group of analytes are being trapped in said reverse-phase column;

h) after said second group of analytes have been trapped in said reverse-phase column, to cause said binary high-pressure pump to introduce a releasing solvent into said reverse-phase column while the eluate from said reverse-phase column is directed to said second chromatographic separation means; and i) to cause said binary high-pressure pump to change the composition of said releasing solvent to separate at least some of said second group of analytes on said second chromatographic separation means.

44. Apparatus as claimed in claim 34 further comprising means for diverting to waste at least some of the eluate from said reverse-phase column while analytes in said intermediate eluate are being trapped therein.

45. Apparatus as claimed in claim 34 wherein said second chromatographic separation means comprises a nanoflow chromatographic column capable of optimally separating at least some of said analytes at a flow rate of less than 1 μl/minute and said first chromatographic separation means comprises a chromatographic column capable of optimally separating at least some of said analytes at a flow rate greater than 1 μl/minute.

46. Apparatus as claimed in claim 45 wherein said reverse-phase column comprises a chromatographic column which is capable of trapping said analytes at a flow rate greater than 1 μl/minute.

47. Apparatus as claimed in claim 34 said second chromatographic trapping means comprises reverse-phase separating media.

\* \* \* \* \*